United States Patent

Rhodes

[11] Patent Number: 5,951,286
[45] Date of Patent: Sep. 14, 1999

[54] DEVICE FOR THE REMOVAL OF INSTALLED DOWEL PINS

[76] Inventor: Charles R. Rhodes, 28536 W. Oviatt St., Bay Village, Ohio 44140

[21] Appl. No.: 09/020,485

[22] Filed: Feb. 9, 1998

[51] Int. Cl.[6] .................................................. A61C 3/02
[52] U.S. Cl. ............................................................ 433/165
[58] Field of Search ............................................. 433/165

[56] References Cited

U.S. PATENT DOCUMENTS

| | | | |
|---|---|---|---|
| 1,123,730 | 1/1915 | Greenfield | 433/165 |
| 1,216,683 | 2/1917 | Greenfield | 433/165 |
| 3,650,032 | 3/1972 | Kestler | 433/53 |
| 3,979,829 | 9/1976 | Lemos | 433/165 |
| 4,412,822 | 11/1983 | Blechner | 433/60 |
| 4,793,806 | 12/1988 | Elledge | 433/74 |
| 4,954,081 | 9/1990 | Williams | 433/53 |
| 5,075,948 | 12/1991 | Maier | 29/264 |
| 5,100,322 | 3/1992 | Weissman | 433/165 |
| 5,285,598 | 2/1994 | Arita et al. | 51/283 |
| 5,571,014 | 11/1996 | Gregory, Jr. et al. | 433/141 |
| 5,575,656 | 11/1996 | Hajjar | 433/165 |
| 5,683,391 | 11/1997 | Boyd | 606/61 |

FOREIGN PATENT DOCUMENTS

| | | | |
|---|---|---|---|
| 661856 | 6/1938 | Germany | 433/165 |

*Primary Examiner*—John J. Wilson
*Attorney, Agent, or Firm*—John D. Gugliotta

[57] ABSTRACT

Disclosed is a device for the removal of dental dowel pins that consists of a hollow boring bit for use with an otherwise conventional dental drill. The inside diameter of the hollow bit is of a size sufficient to accept a dental dowel pin of a conventional size, thus providing a means by which to bore around a dowel in order to remove it from the tooth structure in which it is implanted.

6 Claims, 3 Drawing Sheets

DEVICE FOR THE REMOVAL OF INSTALLED DOWEL PINS

BACKGROUND OF THE INVENTION

1. Field of the Invention

The present invention relates generally to equipment used to remove installed dowel pins and, more specifically, to a specialized dental drill attachment that facilitates the removal of installed dental dowel pins and the like.

2. Description of the Related Art

A common procedure used in reaction to the deterioration of one's teeth is the implantation of tooth-like dental caps. Typically, this procedure involves grinding off the decayed portion of the affected tooth, leaving the root and, perhaps, a small portion of the tooth structure above the gum line in tact and secured within the jaw tissue and bone. A small hole is then drilled vertically, near the center of the remaining portion of the tooth, and a dental dowel pin is placed therein. Secured in the hole by a special dental compound, the dowel pin provides a means by which the dental cap can be attached and secured to the remaining tooth structure.

Occasionally, dental dowel pins can break due to accidents or excessive wear. When this occurs, the common practice is to drill a new hole, near the broken dowel pin, and implant a new one. However, this practice, depending upon the situation, is not always convenient and can sometimes lead to complications. For example, repetitive dowel pin drilling can jeopardize the structural integrity of the remaining tooth portion and may lead to failure, requiring the removal of the entire root. Furthermore, depending upon the tooth size and the extent of the original tooth decay, the amount of original tooth matter available may not be sufficient to accommodate a second hole. Accordingly, the need has arisen for a solution to the aforementioned problems that will provide an effective means by which worn or broken dental dowel pins can be removed from a patient's tooth so that a replacement dowel pin can be installed in the original hole.

In the ancillary art, U.S. Pat. No. 4,954,081, issued in the name of Williams, discloses a dental dowel pin removal device. This device, however, is intended for use in removing the dental dowel pins from a dental cast or a set of dentures, making it inapplicable in the present situation. Furthermore, this device consists of a frame of a size capable of accommodating an entire set of dentures, thereby prohibiting adaptation for purposes similar to that of the present invention.

U.S. Pat. No. 4,412,822, issued in the name of Blechner and U.S. Pat. No. 3,650,032, issued in the name of Kestler, disclose devices used to to set dental dowel pins in dentures and the like. However, these devices do not contemplate the removal of the dowel pins nor are they of a size appropriate for use within the oral cavity, thus they are neither appropriate nor applicable in the present situation.

U.S. Pat. No. 5,075,948, issued in the name of Maier, discloses a minimum clearance dowel extraction tool for use in the removal of metal dowel pins used in the mechanical arts. The device includes a threaded dowel-pulling pin that is bored into the dowel pin itself, anchoring it therein, and thereby allowing for the removal of the dowel by drawing upon the dowel-pulling pin. The Maier disclosure does not anticipate any dental dowel pin applications. Furthermore, it is apparent based upon the design that this device is affective only with dowel pins of some minimum or threshold diameter that is obviously larger than that of conventional dental dowels currently being used.

U.S. Pat. No. 4,793,806, issued in the name of Elledge, discloses a design for a dental dowel pin. However, the disclosure does not anticipate any removal means and the dowel pin is intended primarily for use in dentures and the like.

A search of the previous art did not disclose any patents that read directly on the claims of the instant invention. Consequently, a need has been felt for providing an effective means by which worn or broken dental dowel pins can be removed from a patient's tooth.

SUMMARY OF THE INVENTION

Briefly described according to the preferred embodiment, the present invention is a device for the removal of dental dowel pins and the like that consists of a boring bit for use with a conventional dental drill. The bit consists of a hollow, cylindrical metallic shaft with cutting teeth located around the annular surface of the cutting end. The inside diameter of the hollow bit is of a size sufficient to accept a dental dowel pin of a conventional size, thus providing a means by which to bore around a dowel in order to remove it from the tooth structure in which it is implanted.

It is therefore an object of the present invention to provide a device for the removal of dental dowel pins and the like that is easy to use and effective in removing worn or broken dental dowel pins from teeth.

It is another object of the present invention to provide a device for the removal of dental dowel pins and the like whose use will minimize the risk of damaging the structural integrity of the tooth.

It is another object of the present invention to provide a device for the to removal of dental dowel pins and the like that eliminates the need to drill additional holes in order to repair worn or broken dental dowel pins.

It is another object of the present invention to provide a device for the removal of dental dowel pins and the like that attaches to and is used in conjunction with a conventional dental drilling device.

It is another object of the present invention to provide a device for the removal of dental dowel pins and the like that is of high quality construction using materials that are durable and resistant to dulling.

Finally, it is an object of the present invention to provide a device for the removal of dental dowel pins and the like that is easy to clean and maintain in a sanitary condition.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

LIST OF REFERENCE NUMBERS

Figure 1:
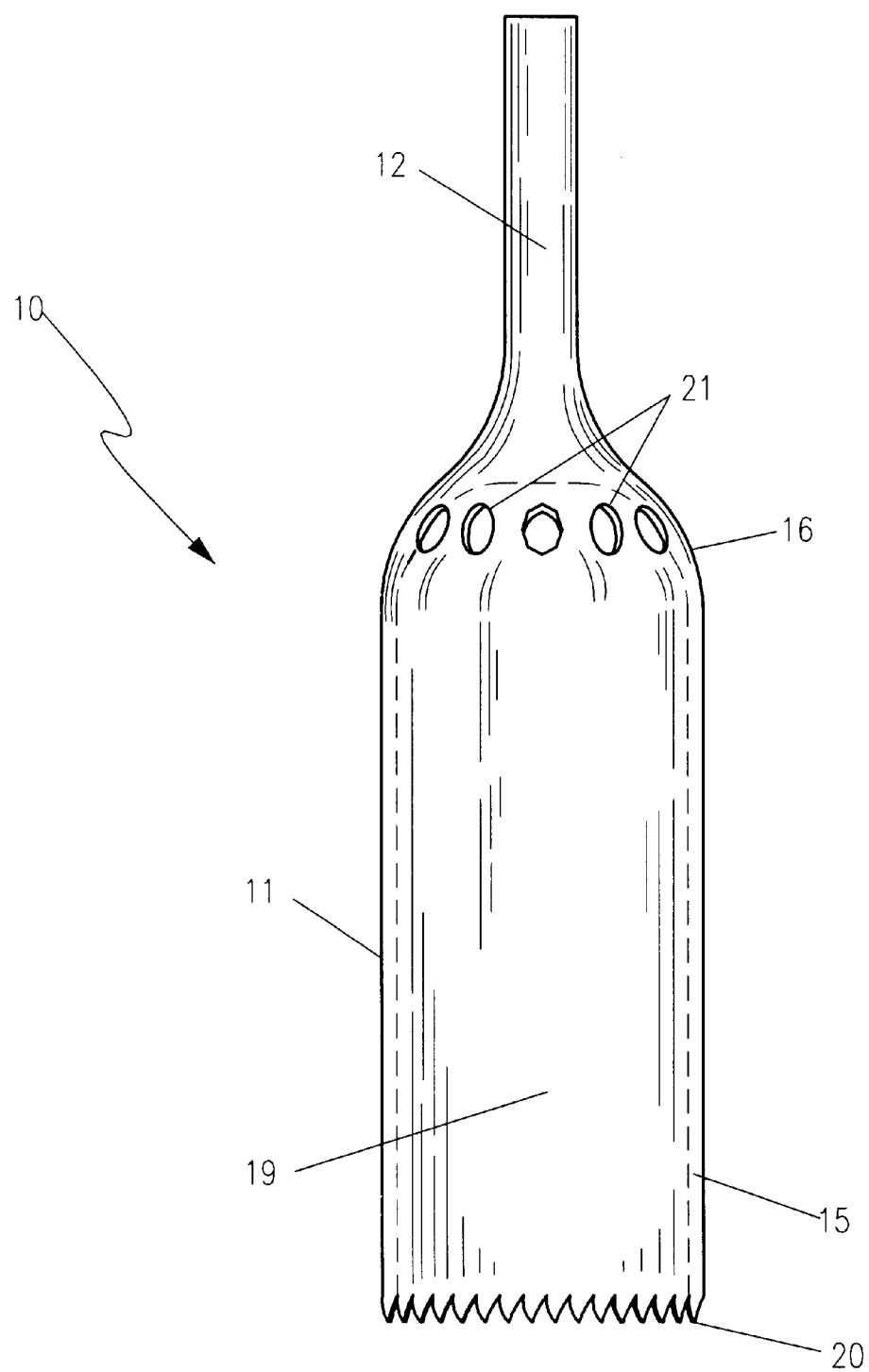
FIG. 1 is a profile view of a device for the removal of dental dowel pins and the like according to the preferred embodiment of the present invention.
Figure 2:
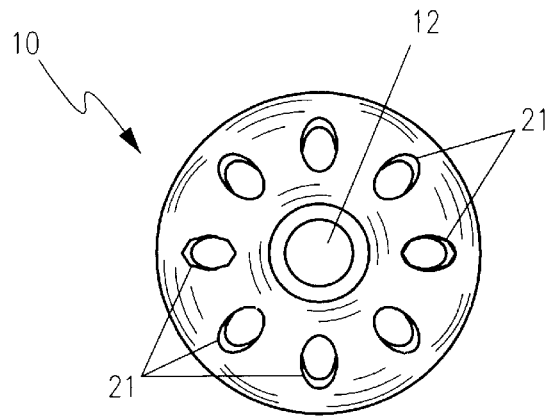
FIG. 2 is a top view of a device for the removal of dental dowel pins and the like according to the preferred embodiment of the present invention.
Figure 3:
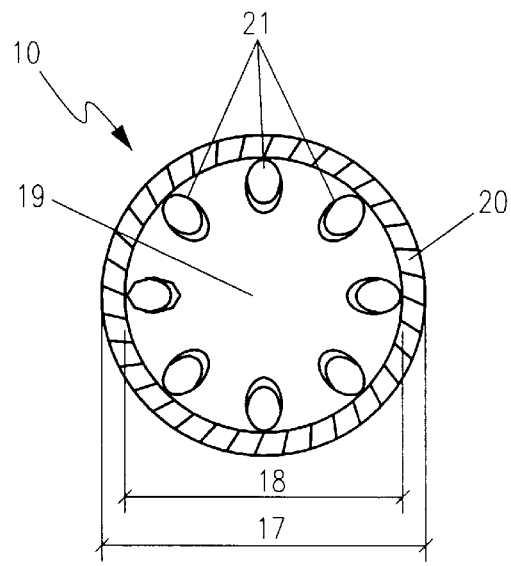
FIG. 3 is a bottom view of a device for the removal of dental dowel pins and the like according to the preferred embodiment of the present invention.
Figure 4:
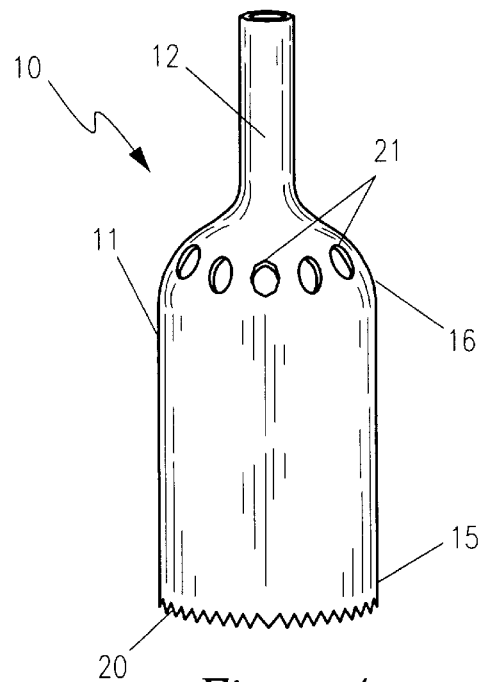
FIG. 4 is a perspective view of a device for the removal of dental dowel pins and the like according to the preferred embodiment of the present invention.

10 Dowel Removal Device
11 Boring Body
12 Drill Attaching Stem
15 Cutting End
16 Stem End
17 Outside Diameter
18 Inside Diameter
19 Cylindrical Interior Cavity
20 Angular Dentendes
21 Cleaning Ports
25 Conventional Dental Drill
26 Dental Dowel Pin
27 Tooth Root Structure

DESCRIPTION OF THE PREFERRED EMBODIMENTS

In order to describe the complete relationship of the invention, it is essential that some description be given to the manner and practice of functional utility and description thereof. Accordingly, the best mode for carrying out the invention is presented in terms of its preferred embodiment, herein depicted within the figures.

1. Detailed Description of the Figures

Referring now to FIG. 1, FIG. 2, FIG. 3 and FIG. 4, depicted is a device for the removal of dental dowel pins and the like 10, hereinafter dowel removal device. The dowel removal device 10 is machined from a single piece of material and consists of a boring body 11 portion and a drill attaching stem 12 portion, hereinafter stem. Although in its preferred embodiment the dowel removal device is envisioned as being formed of a single piece of material, it is also envisioned that one skilled in the art, in conjunction with the teachings of the present disclosure, could achieve similar features and benefits utilizing a multicomponent structure. The boring body 11, generally cylindrical in shape with a cutting end 15 opposed to a stem end 16, is of an outside diameter 17, hereinafter O.D., not exceeding ⅛ inches and an inside diameter 18, hereinafter I.D., greater than that of a conventional dental dowel pin. The boring body 11 contains a hollow, cylindrical interior cavity 19 extending the length thereof and of a diameter sufficient to accept a conventional dental dowel pin while maintaining an annular clearance there around. It is envisioned that the interior cavity 19 could have provided along its surface a friction reduction means, such as a Teflon (tm) coating or similar method. The stem 12 is generally cylindrical in shape and solid throughout with a diameter smaller than that of the boring body 11, yet sufficient to be accepted by and secured within a conventional dental drill bit securing means, such as a three prong, drill chuck-type device wherein the prongs are actuated by rotating a threaded sleeve that forces the prongs to converge upon the bit, thus securing it therein. The dowel removal device 10 is formed so as to achieve a contoured transition between the stem 12 portion and the boring body 11 portion.

Angular dentendes 20, are located around the annular edge of the cutting end 15 of the boring body 11 and form a series of linearly aligned, radially curving cutting teeth. The angular dentendes 20 are oriented such that, when the dowel removal device 10 is used with a conventional dental drilling device, the rotational motion of the angular dentendes 20 will bore a circular channel in a direction parallel to the longitudinal axis of the dental removal device 10, leaving the material within the cylindrical interior cavity in tact.

The material used to construct the dowel removal device 10, due to its specialized use according to the preferred embodiment, must be of a suitable strength and hardness to facilitate cutting tooth enamel. Accordingly, the dowel removal device 10 will be constructed of a high strength/hardness stainless steel alloy and may include special cutting provisions such as diamond or carbide-tipped blades, as are otherwise available within the art of dental tools.

A plurality of cleaning ports 21 are positioned in a linear fashion around the boring body 11 near the stem end 16. It is also envisioned that an alternate embodiment containing a single, central cleaning shaft may also be effective in achieving the desired ability to remove dust and debris from the cutting surface. The cleaning ports 21 consist of apertures, circular in shape, that provide a fluid connectivity between the outer surface of the boring body 11 and the cylindrical interior cavity 19 and are angled acutely relative to the longitudinal axis of the dowel removal device 10. As shavings are created during boring procedures, they tend to accumulate inside the cylindrical interior cavity 19. The cleaning ports 21 facilitate removal of the shavings by providing a means by which they can be forced out by blowing air, washing with a cleaning solution or by the insertion of a rigid cleaning utensil.

An alternate embodiment of the present invention involves the use of the dowel removal device 10 to dislodge a variety of dowel pin-like objects in the medical field, such as broken surgical pins, screws and the like, and ordinary objects such as nails, screws, rivets and the like. The alternate embodiments do not materially alter the design of the dowel removal device 10 other than varying the diameter of the device, depending upon the application, and varying the size/shape of the attaching stem 12 in order to accommodate varying drive devices. Furthermore, special coatings may be utilized in order to reduce friction/abrasion and special features such as fluting or rifling may be used in specialized situations to enhance the removal of material. Finally, the materials used in the construction of the dowel removal device 10 may be altered, depending on the materials being removed, and include most common steel, aluminum and other alloy metals.

2. Operation of the Preferred Embodiment

Figure 5:
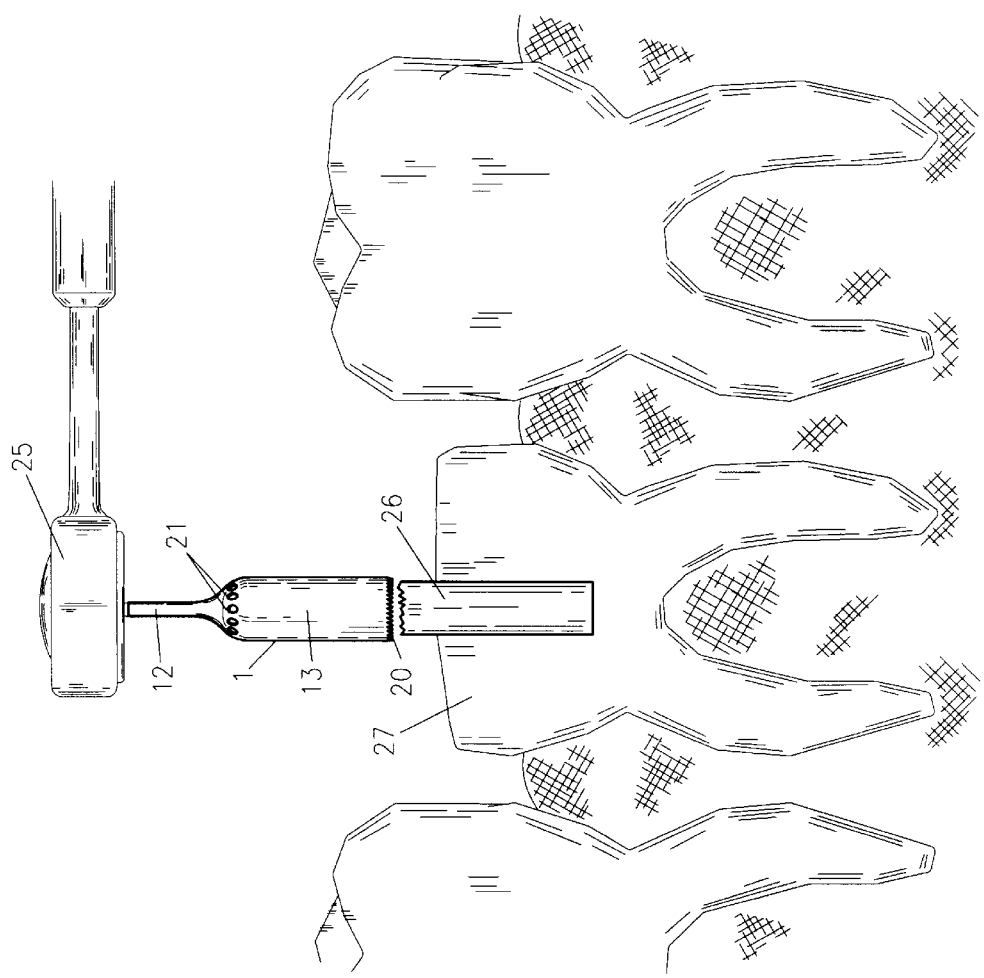
FIG. 5 is a profile view of a device for the removal of dental dowel pins and the like depicting its use according to the preferred embodiment of the present invention.

In accordance with the preferred embodiment of the present invention, FIG. 5 depicts the use of the dowel removal device 10 in conjunction with a conventional dental drill 25 to remove a broken dental dowel pin 26, hereinafter dental dowel pin, from a tooth root structure 27.

By positioning the dowel removal device 10 such that the cylindrical to interior cavity 19 surrounds the dental dowel pin 26 implanted in a patient's tooth root structure 27, the material surrounding the dental dowel pin 26 can be bored away, leaving the dental dowel pin 26 in tact so that it can be removed, easily and gently, with a pair of pliers or the like. The gentle removal of the pin is critical in order to maintain the structural integrity of the tooth root structure.

Once the boring-out process is completed, the material accumulated in the cylindrical interior cavity 19 can be forced out by use of the cleaning ports 21 in the aforementioned manner. Furthermore, the materials used to construct the dowel removal device 10 allow for cleaning, disinfecting and sterilization methods commonly used in the medical fields.

In the alternate embodiments, the fact that the dowel removal device 10 is used in a wide variety of situations and with a wide variety of drive devices to remove dowel pin-like members from implantation within differing materials, does not alter the method in which it is used.

While the preferred embodiments of the invention have been shown, illustrated, and described, it will be apparent to those skilled in this field that various modifications may be made in these embodiments without departing from the spirit of the present invention. It is for this reason that the scope of the invention is set forth in and is to be limited only by the following claims.

What is claimed is:

1. A device for removing dental dowel pins installed in a tooth root structure, said dowel removal device comprising:

a boring body, generally cylindrical and elongated in shape, with a cutting end opposite a stem end, and a hollow interior cavity, said boring body having an outside diameter defined by the outer surface of said boring body, and an inside diameter defined by said hollow interior cavity formed within said boring body, said hollow interior cavity being generally elongated, cylindrical and lies along the longitudinal axis of said boring body, in fluid connectivity with said cutting end, extending the length of said boring body, ending prior to said stem end, a distance no greater that one quarter the length of said boring body, thus preventing fluid connectivity therewith, said hollow interior cavity being coated with a friction reduction material;

a plurality of cleaning ports, said cleaning ports positioned in a linear fashion around said boring body near said stem end;

a drill attachment stem, generally cylindrical and elongated in shape, said drill attachment stem connected to said stem end of said boring body and extending along the same longitudinal axis as said boring body; and a cutting edge, said cutting edge located at said cutting end of said boring body, said cutting edge being formed of a series of aligned diamond chips.

2. A device for removing dental dowel pins installed in a tooth root structure as described in claim 1, wherein said dowel removal device is formed of a single piece of material.

3. A device for removing dental dowel pins installed in a tooth root structure as described in claim 1, wherein said drill attachment stem is of a diameter sufficient to attach said dowel removal device to a conventional dental drill bit securing mechanism.

4. A device for removing dental dowel pins installed in a tooth root structure as described in claim 1, wherein said cleaning ports comprise a plurality of apertures that are circular in shape and provide fluid connectivity between said outer surface of said boring body and said hollow interior cavity and are angled acutely relative to the longitudinal axis of said dowel removal device.

5. A device for removing dental dowel pins installed in a tooth root structure as described in claim 1, wherein said cutting edge comprises a series of angular dentendes, said series of dentendes forming a series of linearly aligned, radially curving cutting teeth.

6. A device for removing dental dowel pins installed in a tooth root structure as described in claim 1, wherein said drill attachment stem is of a diameter and configuration sufficient to attach said dowel removal device to a rotational drive mechanism.

* * * * *